United States Patent [19]

Pollack et al.

[11] 4,021,540
[45] May 3, 1977

[54] PREPARATION OF A HEPATITIS B IMMUNE GLOBULIN AND USE THEREOF AS A PROPHYLACTIC MATERIAL

[75] Inventors: William Pollack, Belle Mead; Albert McKee, Flemington, both of N.J.

[73] Assignee: Ortho Diagnostics Inc., Raritan, N.J.

[22] Filed: July 28, 1975

[21] Appl. No.: 599,619

[52] U.S. Cl. .................................. 424/86; 424/12; 260/112 R; 260/112 B
[51] Int. Cl.[2] ........................................ A61K 39/42
[58] Field of Search ............... 424/86, 12; 260/112

[56] References Cited
OTHER PUBLICATIONS

Tullis, "Blood Cells & Plasma Proteins", Academic Press Inc., NY, 1953, pp. 21,30.

*Primary Examiner*—Lewis Gotts
*Assistant Examiner*—Cary Owens

[57] ABSTRACT

A method for producing a novel immunizing agent is described. The immunizing agent is anti-$HB_s$ gamma globulin essentially free of fibrinogen, plasminogen, 19 S globulin and lipids found to be effective in immunizing against hepatitis B virus disease. The method of producing this material involves fractionation of human plasma utilizing selective solvent and control of pH, temperature and ionic strength.

7 Claims, 1 Drawing Figure

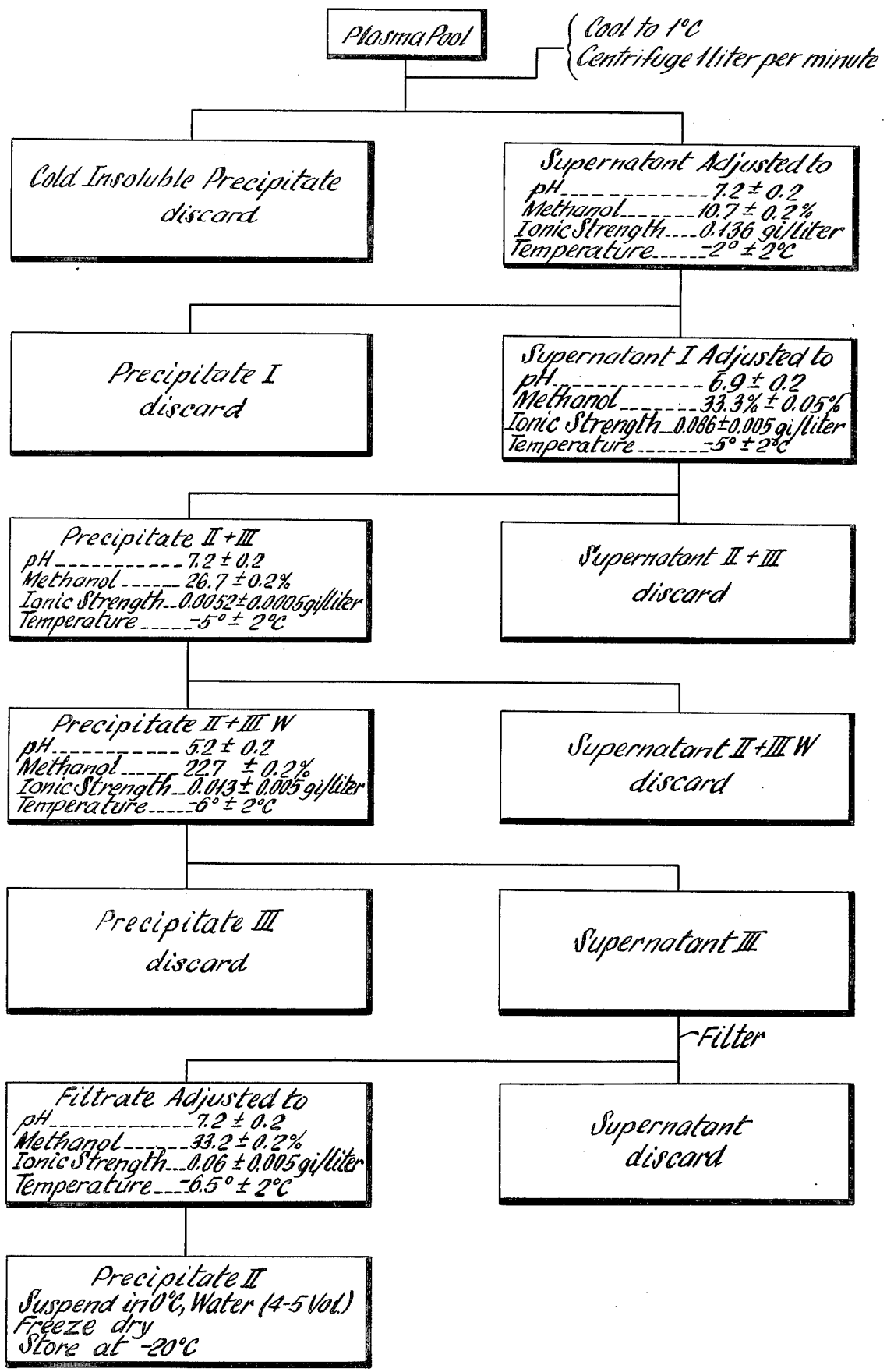

PREPARATION OF A HEPATITIS B IMMUNE GLOBULIN AND USE THEREOF AS A PROPHYLACTIC MATERIAL

This invention relates to the production of a novel gamma globulin and more particularly to a method for producing a novel specific hyper immune gamma globulin designated Hepatitis B immune globulin.

Since its first reported use in 1945 by Neefe, J. R., and Stokes, J. Jr. in the *Journal of the American Medical Association*, 145, 128, 1063, almost all normal human immune globulin preparations have been of value in the prophylaxis of type A hepatitis. Normal globulin has been recommended for routine use for the prevention of secondary cases among exposed household contacts. Only occasional lots have appeared to be substandard in efficiency for this purpose.

In contrast, however, the value of such normal globulin preparations for prophylaxis of hepatitis B virus (HBV) infection has long been in question. See for example Mosley, J. W., Galambos, J. T., Diseases of the Liver (edited by L. Schiff); p. 410, Philadelphia, 1969 and National Academy of Sciences - National Research Council Committe on Viral Hepatitis, *Morbidity and Mortality Weekly Report*, 1972, 21, 133. The differing conclusions from the various investigations of effectiveness of normal globulin preparations in preventing type B hepatitis may have resulted from a number of factors, including variations in the concentration of specific antibodies (anti-$HB_s$) in the lots used, and the unreliability of diagnosis in studies prior to hepatitis B surface antigen ($HB_sAg$) testing. It is widely agreed, however, that effective prophylaxis with normal globulin is too inconsistent to justify any recommendation that it be used in attempts to prevent type B disease.

The ability specifically to diagnose type B hepatitis brought recognition that continued close contact with carriers can result in intra-household transmission, and this has all the more spurred interest in obtaining an immune globulin that could effectively immunize against the B type of the disease.

This invention therefore provides such a material as well as a method for producing it and utilizing it in the immunization of susceptible hosts.

GENERAL DESCRIPTION OF THE INVENTION

The novel anti-$HB_s$ immune gamma globulin of the present invention is pure and is essentially free of fibrinogen, 19 S globulin, plasminogen and lipids. It is prepared from human plasma containing preferably a high titre of that antibody. It is well within the skill of the art to identify and obtain such plasma as a starting material. As is known, human plasma contains many components such as albumin, plasminogen, alpha, beta and gamma globulins and various lipids. The fractionation of such material to obtain the desired component in accordance with the present invention is dependent upon the solubility of various components of the plasma at various stages and under different conditions.

At each stage of the fractionation, the separation of the fraction and the ultimate removal of those components which are undesirable in the anti-$HB_s$ globulin are determined by the critical control of pH, temperature, concentration of the precipitant and the ionic strength of the system. The invention therefore utilizes a series of steps to effect the removal of those components which are undesirable via control of conditions which alter the solubility of those components.

Various organic solvents of low dielectric constant such as ketones and alcohols precipitate proteins and have been used in the fractionation of plasma. The organic solvent utilized in the method of this invention is preferably methanol, although other lower alkanols such as ethanol and propanol may be used. The ability to maintain the critical ionic strengths at the various stages of the fractionation is facilitated by the use of methanol. When other solvents are used, appropriate changes in process conditions as they affect solubility will be made.

In order to prevent denaturation of the proteins during fractionation, precipitation is carried out at low temperatures. Since protein solubility is temperature dependent, the temperature chosen for each step of the fractionation should for reasons of economy be the lowest possible which permits the desired separation in order to prevent denaturation.

Referring to the flowsheet, the fractionation proceeds from whole human plasma. The plasma is cooled to about 0°–5° C. and is then centrifuged to separate a cold insoluble precipitate from a supernatant. The supernatant is further fractionated to yield Precipitate I and Supernatant I. Precipitate I which consists principally of fibrinogen is discarded. Supernatant I is further fractionated to yield Supernatnat II + III and Precipitate II + III. Supernatant II + III, which is discarded, contains alpha and beta globulin and lipids. Precipitate II + III consists principally of beta and gamma globulins and isoagglutinins, but also contains prothrombin, plasminogen, cholesterol and other lipids. Precipitate II + III, upon further frationation yield Supernatant II + III W and Precipitate II + III W. The beta globulin, cholesterol and other lipids are largely removed in Supernatant II + III W which is discarded. Precipitate II + III W consists principally of gamma globulins, isoagglutinins, plasminogen and prothrombin and some beta globulin, cholesterol and other lipids. Upon further fractionation, Precipitate (II + III W yields Supernatant III + Precipitate III. Precipitate III, which is discarded, contains isoagglutinins, plasminogen and prothrombin. Supernatant III consists principally of gamma globulins and minor amounts of fibrinogen and lipids. The final step of the fractionation yields Precipitate II which is essentially pure anti-$HB_S$ immune gamma globulin almost completely free of 19 S globulin, plasminogen and lipids.

The invention may be more fully understood with reference to the following example.

EXAMPLE I

Human blood plasma having an anti-$HB_s$ titre of about 6000 is cooled to 1° ± 1° C. The plasma is centrifuged in a Sharpless Super-Centrifuge with a 3-wing in bowl, at 1° ± 1° C. feeding at the rate of 1000 ± 50 ml. per minute. The cold insoluble precipitate is discarded. The pH of the supernatant is adjusted to 7.2 ± 0.2. The methanol content of the batch is brought to 10.7 ± 0.1% (v./v.) by the addition of 177 ml. of 71% (v./v.) methanol per liter of plasma. The solution is stirred slowly at −5° ÷ 0.5° C. for one hour and is maintained at −5° ÷ 0.5° C. overnight. The solution is centrifuged in a Sharples Super-Centrifuge with a 3-wing in bowl at −5° ± 0.5° C., feeding at the rate of 1000 ± 100 ml. per minute. Supernatant I is collected in a bowl equipped with cooling device.

To each liter of Supernatant I there is added, with cooling, 601 ml. of 71% (v./v.) methanol, 0.88 ml. of 10 N acetic acid, and 0.44 ml. of 4 N sodium acetate. This brings the methanol concentration of 33.3%, the ionic strength to 0.086 gi./liter and the pH to 6.9. The solution is brought to a temperature of $-5° \pm 0.5°$ C. and is stirred slowly for 2 hours. The solution is then allowed to stand at $-5.5° \pm 0.5°$ C. for 16 hours.

The solution is centrifuged in a Sharpless Super-Centrifuge with a 3-wing in bowl at $-5° \pm 0.5°$ C., at a rate of 1000 ml. $\pm$ 100 ml. per minute. Precipitate II + III is removed from the bowl, weighed, and is stored at a temperature of $-20°$ C.

Maintaining a temperature of 0°., Precipitate II + III is suspended in 2 volumes (2 times original weight of Precipitate II + III) of 0° C. water in equilibrium with ice by cutting up the paste with a stainless steel spatula in a stainless steel pot and stirring until the suspension is uniform. Three volumes (3 times original weight of Precipitate II + III) of 0.0187 M disodium phosphate solution is added to the suspension with stirring. Twenty volumes (20 times original weight of Precipitate II + III) of water at 0° C. is added and the stirring at 0° C. is continued for 30–60 minutes. The pH is 7.2 $\pm$0.2. To obtain a methanol percentage of 26.7$\pm$0.2%, 15 volumes (15 times the original weight of Precipitate II $\pm$ III) of 71% (v./v.) methanol at $-10°$ C. is added. The ionic strength of the solution is 0.0052 $\pm$ 0.0005 gi./liter.

The solution is brought to a temperature of $-5°$ C. and is centrifuged in the Sharpless Super-Centrifuge with a 3-wing in bowl at a temperature of $-5.5° \pm 0.5°$ C. at a rate of 500 $\pm$ 50 ml. per minute. Precipitate II + III W is removed from the bowl and is weighed.

Precipitate II + III W is suspended in 2 volumes (2 times weight of Precipitate II + III W) of ice water. To the suspension is added 2 volumes (2 times weight of Precipitate II + III W) of 0.175 M sodium acetate. A further 1 volume (1 times weight of Precipitate II + III W) of ice water containing 0.216 ml. of acetate buffer for each gram of Precipitate II + III W paste. The acetate buffer is prepared by diluting 40 ml. of 10 N acetic acid and 20 ml. of 4 N sodium acetate to 100 ml. with distilled water. The pH of the solution is 5.2 $\pm$0.2. The solution is stirred slowly for one hour. There is then added 13.5 volumes (13.5 times the original weight of Precipitate II + III W) of ice water and 8.66 volumes (8.66 times the original weight of Precipitate II + III W) of 71% (v./v.) methanol while maintaining the temperature at $-6°\pm 0.5°$ C. The solution is stirred slowly for one hour and is allowed to stand overnight. The solution contains 22.7% methanol and has a pH of 5.2 and an ionic strength of 0.015 gi./liter.

The solution is centrifuged in a Sharpless Super-Centrifuge with a 3-wing in bowl, at a temperature of $-6° \pm 0.5°$ C., and at a flow rate of 500 $\pm$ 50 ml. per minute. The volume of Supernatant III is measured. Precipitate III is discarded.

Supernatant III is treated with 0.4% w./v. Celite 512 and is stirred for 20 minutes. The mixture is filtered through an Eitel filter press containing D-8 pads.

An acetate buffer of pH 5.2 is made up as follows: 25 ml. 4 N sodium acetate and 3 ml. 10 N acetic acid mad eup to 100 ml. with distilled water. The accetate buffer is diluted 100 times with 22.7% methanol. This solution has an ionic strength of 0.01 gi./liter. An Eitel filter press is precoated with the acetate buffer plus Celite 512 (0.5 gm./square inch of pad surface) using 40 ml. of acetate-methanol buffer/square inch of pad surface. Supernatant III is filtered and to the filtrate is added 50 millimoles (2.923 grams) of sodium chloride and 7.65 ml. of 1 M sodium bicarbonate per liter of filtered Supernatant III. The pH of the filtrate is 7.2 $\pm$ 0.2.

To the filtrate is added 160 volumes of 100% methanol at a temperature below $-5°$ C. The mixture is stirred slowly for 1 hour at a temperature of $-6.5° \pm 0.5°$ C. The mixture is permitted to stand overnight.

The solution is centrifuged in a Sharples Super-Centrifuge with 3-wing in bowl, at a temperature of $-6° \pm 0.5°$ C. and at a flow rate of 500 $\pm$ 50 ml. per minute. The supernatant is discarded.

Precipitate II is removed, suspended in 4 volumes of ice water and freeze-dried. The freeze-dried powder is weighed and is stored below at a temperature of $-5°$ C.

Precipitate II as prepared by this example is 99% pure anti-$HB_s$ immune gamma globulin free from plasminogen, fibrinogen, lipids and 19 S globulins.

EXAMPLE II

Two human immune globulins were prepared as 13.5 $\pm$ 1.5 gm./dl. solutions by the procedure of Example I. The human plasma starting material was derived from plasma units known to contain anti-$HB_s$ in moderate to high titres by passive hemagglutination. The control globulin was derived from plasma units with no anti-$HB_s$ detectable by passive hemagglutination. Both immune globulin preparations were dispensed as 5 ml. volume into identical, single-dose vials coded with a randomly assigned two-digit designation. Both preparations met all applicable standards for "Immune Globulin (Human)" of the Bureau of Biologics, Food and Drug Administration, U.S. Department of Health, Education and Welfare. The hepatitis B immune globulin contained 441 $\mu$g. of specific anti-$HB_s$/ml. by a quantitative solid-phase radioimmunoassay. Its anti-$HB_s$ titre by passive hemagglutination was 1:200,000 and 1:150,000, respectively, against cells coated with the $HB_s$Ag subtypes adw and ayw.

During the 29 month period from July, 1972 to December, 1974, 96 human propositi were identified as having icteric hepatitis, with symptoms, signs and laboratory findings compatible with acute viral hepatitis and a positive test for $HB_s$Ag confirmed by subtyping or specificity. During this period, these propositis exposed a total of 100 sexual partners with whom they lived during the period spanning two weeks to two months prior to onset. Two treatment groups were formed from the spouses of these propositis, and a single intramuscular injection of 5ml. of the anti-$HB_s$ immune globulin prepared as described above was given. Additional criteria for the spouse included no history of prior hepatitis or jaundice or chronic liver disease, nonusers of injectables, no history of transfusion within 6 months and availability for follow-up during subsequent ten months.

Among the 100 spouses, 47 were randomly allocated to the treated group and 53 to the control group. Due to exclusions of one type or another, 33 remain for analysis in the treated group and 40 in the control group. As of the present time, 58 of the 73 eligible spouses have been studied for 150 days or more post-injection of the globulin of the present invention.

Intervals from recognition of the jaundice in the propositi to injection of the spouses ranged from 7 days before to 30 days after with a median of 9 days. In all, there were 11 cases of hepatitis reported in the spouses, of which 9 were icteric. Nine cases of hepatitis B disease occurred in the control group and none in the spouses treated with the hepatitis B immune globulin of this invention.

As used in this study, icteric hepatitis was defined as suspected jaundice of the skin or eyes confirmed by a serum bilirubin level of 2 mg. per dl. or higher. Anicteric hepatitis was defined as symptomatic hepatitis confirmed by appropriate levels and patterns of serum aminotransferase activities, but without a serum bilirubin observed to be as high as 2.0 mg./dl. Both icteric and anicteric forms of symptomatic hepatitis were defined as type B disease on the basis of the following criteria: (1) de novo appearance of $HB_sAg$; (2) de novo appearance of anti-$HB_s$ in recipients of control globulin; (3) a declining titre of anti-$HB_s$ after hepatitis immune globuin injection, followed by a four-fold or greater increase. Symptomatic cases failing to meet these criteria were classified as "non-B" hepatitis.

An effective amount of the material of the present invention suitable in preventing the incidence of hepatitis B viral disease in susceptible host ranges preferably from 25 to 50 µg. of specific anti-$HB_s$/ml. per kg. of body weight. The material is administered parenterally and preferably intramuscularly in a single dose injection.

What is claimed is:

1. An essentially pure anti-$HB_s$ gamma globulin being essentially free of plasminogen, fibrinogen, lipids and 19 S globulins.

2. The method of immunizing against the incidence of hepatitis B viral disease which comprises parenterally administering to a susceptible host an effective amount of an essentially pure anti-$HB_s$ gamma globulin essentially free of plasminogen, fibrinogen, lipids and 19 S globulins.

3. The method according to claim 2, wherein the anti-$HB_s$ gamma globulin is administered intra-muscularly.

4. The method according to claim 3 wherein the amount of anti-$HB_s$ gamma globulin administered corresponds to 25 to 50 micrograms of specific anti-$HB_s$ per kilogram of host body weight.

5. The method according to claim 4 wherein the anti-$HB_s$ gamma globulin administered contains approximately 442 micrograms of specific anti-$HB_s$ per ml. measured by quantitative solid phase radioimmunoassay.

6. The gamma globulin of claim 1 wherein the gamma globulin is derived from a high titre anti-$HB_s$ human source plasma.

7. The anti-$HB_s$ gamma globulin of claim 6 having a specific $HB_s$ antibody titre of at least 442 micrograms per ml. by quantitative radioimmunoassay.

* * * * *